United States Patent
Michaelis et al.

(10) Patent No.: US 8,117,087 B2
(45) Date of Patent: Feb. 14, 2012

(54) CUSTOMER LOYALTY, PRODUCT DEMONSTRATION, AND STORE/CONTACT CENTER/INTERNET COUPLING SYSTEM AND METHOD

(75) Inventors: Paul Roller Michaelis, Louisville, CO (US); David S. Mohler, Arvada, CO (US)

(73) Assignee: Avaya Inc., Basking Ridge, NJ (US)

( * ) Notice: Subject to any disclaimer, the term of this patent is extended or adjusted under 35 U.S.C. 154(b) by 0 days.

(21) Appl. No.: 12/566,395

(22) Filed: Sep. 24, 2009

(65) Prior Publication Data

US 2011/0071884 A1 Mar. 24, 2011

(51) Int. Cl.
*G06Q 30/00* (2006.01)
(52) U.S. Cl. ..................... 705/26.9; 705/26.1
(58) Field of Classification Search ............. 705/26, 705/27
See application file for complete search history.

(56) References Cited

U.S. PATENT DOCUMENTS

| | | | |
|---|---|---|---|
| 5,185,695 A | 2/1993 | Pruchnicki | |
| 5,502,636 A | 3/1996 | Clarke | |
| 5,970,469 A | 10/1999 | Scroggie et al. | |
| 6,041,309 A | 3/2000 | Laor | |
| 6,134,593 A * | 10/2000 | Alexander et al. | 709/229 |
| 6,151,643 A * | 11/2000 | Cheng et al. | 710/36 |
| 6,832,230 B1 * | 12/2004 | Zilliacus et al. | 455/414.3 |
| 7,054,832 B1 * | 5/2006 | Vallabh | 705/26 |
| 7,710,912 B1 * | 5/2010 | Myles et al. | 370/328 |
| 2001/0029607 A1 * | 10/2001 | Veres et al. | 717/11 |
| 2002/0032768 A1 * | 3/2002 | Voskuil | 709/224 |
| 2003/0032417 A1 * | 2/2003 | Minear et al. | 455/419 |
| 2004/0122685 A1 * | 6/2004 | Bunce | 705/1 |
| 2004/0181459 A1 * | 9/2004 | Wright | 705/26 |
| 2004/0260598 A1 * | 12/2004 | Kumhyr et al. | 705/10 |
| 2005/0132358 A1 * | 6/2005 | Peev et al. | 717/174 |
| 2006/0075001 A1 * | 4/2006 | Canning et al. | 707/203 |
| 2006/0206395 A1 * | 9/2006 | Vallabh | 705/26 |
| 2006/0273920 A1 * | 12/2006 | Doan et al. | 340/825.29 |

(Continued)

OTHER PUBLICATIONS

Pacarille, L., "Online Software Buying Drops a few Hurdles" Jun. 22, 1997 Computerworld, vol. 31, issue 22, pp. 47-48.*
Pacarille, L., "Online Software Buying Drops a few Hurdles", ComputerWorld, Jun. 2, 1997, vol. 31, iss. 22, p. 47.*
BNET; Business Wire; "Rewards Programs Pay for Customer Loyalty, But Fail to Engage, According to Allegiance, Inc"; http://findarticles.com/p/articles/mi_m0EIN/is_2008_Feb_28/ai_n24354192/; Feb. 28, 2008; printed Nov. 16, 2009.
Lamalfa, "Buying Loyalty: Do Rewards Programs Translate Into Customer Engagement?" Allegiance™, 2008, 8 pages.

(Continued)

*Primary Examiner* — Adam Levine
*Assistant Examiner* — Ethan D Civan
(74) *Attorney, Agent, or Firm* — Sheridan Ross P.C.

(57) ABSTRACT

A system for storing information about searches and inquiries by a customer is provided. The system includes a customer service server that receives information from two or more sources, such as from a retail location sales agent, a website, a call center agent, etc. The information is associated and correlated to interrelate inquiries from the different sources. Further, when the user enters a retail location, a node or server at the retail location can push test application to a user's mobile device based on the past inquiries. These test applications are provided only when the customer is present in the retail location. As such, hacking the application is prevented. Further, with the customer using the application in the retail location, a sales agent is present to assist the customer.

15 Claims, 10 Drawing Sheets

U.S. PATENT DOCUMENTS

| | | |
|---|---|---|
| 2007/0156529 A1* | 7/2007 | Walker et al. .................. 705/14 |
| 2007/0192182 A1* | 8/2007 | Monaco et al. ................ 705/14 |
| 2007/0278288 A1 | 12/2007 | Simmons |
| 2007/0299701 A1* | 12/2007 | Boyer et al. ..................... 705/5 |
| 2008/0103909 A1 | 5/2008 | Huang et al. |
| 2008/0167962 A1 | 7/2008 | Lawe |
| 2008/0281670 A1* | 11/2008 | Boss et al. ..................... 705/10 |
| 2009/0006196 A1* | 1/2009 | Barkan et al. ................. 705/14 |
| 2009/0048917 A1 | 2/2009 | Blake et al. |
| 2009/0125386 A1 | 5/2009 | Willison et al. |
| 2009/0125442 A1* | 5/2009 | Otto et al. ....................... 705/39 |
| 2009/0216549 A1* | 8/2009 | Causey et al. ..................... 705/1 |
| 2009/0276250 A1* | 11/2009 | King et al. ......................... 705/5 |
| 2010/0029254 A1* | 2/2010 | Libonati et al. ............ 455/414.2 |
| 2010/0094529 A1* | 4/2010 | Gupta et al. ................... 701/117 |
| 2010/0208644 A1* | 8/2010 | Ghosn .......................... 370/315 |

* cited by examiner

CUSTOMER LOYALTY, PRODUCT DEMONSTRATION, AND STORE/CONTACT CENTER/INTERNET COUPLING SYSTEM AND METHOD

BACKGROUND

Businesses often keep information about the purchases made by a customer. For example, a retailer with a website may maintain data about past purchases on the website. In another example, retailers with loyalty programs may use the loyalty number to track the purchases of a customer at a retail location. However, these collections of data are often not correlated between different types of customer activity. For example, purchases on a website are often not correlated with purchases at retail locations. Further, businesses generally cannot or do not store information about searches but only stores information about purchases.

Without the information about searches and purchases from other customer activity, businesses are unable to determine the effectiveness of cross-selling between different customer activity. For example, how often does a customer search for information about a product on the Internet then go to a retail location to purchase the product. Or, how often does a user investigate a product in a store only to buy the product on a website. Further, opportunities are lost for businesses to promote products that are researched by the customer.

Generally, to test software applications, a user must download a test application to a computer system. Thus, if a user wants to research a software purchase, the user needs to test the application on his or her computer system. These test applications are often offered for a limited time unless a registration key is provided. After some limited amount of time, the test application is uninstalled or modified to make the test application unusable. However, these test applications are often hacked, and the nefarious user can use the application without purchasing the application. Further, the user has no help or other guidance when using the test application in this way.

SUMMARY

It is with respect to the above issues and other problems that the embodiments presented herein were contemplated. Herein, a system for storing information about searches and inquiries by a customer is provided. The system includes a customer service server that receives information from two or more sources, such as from a retail location sales agent, a website, a call center agent, etc. The information is associated and correlated to interrelate inquiries from the different sources. Further, when the user enters a retail location, a node or server at the retail location can push test application to a user's mobile device. These test applications are provided only when the customer is present in the retail location. As such, hacking the application is prevented. Further, with the customer using the application in the retail location, a sales agent is present to assist the customer.

The phrases "at least one", "one or more", and "and/or" are open-ended expressions that are both conjunctive and disjunctive in operation. For example, each of the expressions "at least one of A, B and C", "at least one of A, B, or C", "one or more of A, B, and C", "one or more of A, B, or C" and "A, B, and/or C" means A alone, B alone, C alone, A and B together, A and C together, B and C together, or A, B and C together.

The term "a" or "an" entity refers to one or more of that entity. As such, the terms "a" (or "an"), "one or more" and "at least one" can be used interchangeably herein. It is also to be noted that the terms "comprising", "including", and "having" can be used interchangeably.

The term "automatic" and variations thereof, as used herein, refers to any process or operation done without material human input when the process or operation is performed. However, a process or operation can be automatic, even though performance of the process or operation uses material or immaterial human input, if the input is received before performance of the process or operation. Human input is deemed to be material if such input influences how the process or operation will be performed. Human input that consents to the performance of the process or operation is not deemed to be "material".

The term "computer-readable medium" as used herein refers to any tangible storage that participates in providing instructions to a processor for execution. Such a medium may take many forms, including but not limited to, non-volatile media, volatile media, and transmission media. Non-volatile media includes, for example, NVRAM, or magnetic or optical disks. Volatile media includes dynamic memory, such as main memory. Common forms of computer-readable media include, for example, a floppy disk, a flexible disk, hard disk, magnetic tape, or any other magnetic medium, magneto-optical medium, a CD-ROM, any other optical medium, punch cards, paper tape, any other physical medium with patterns of holes, a RAM, a PROM, and EPROM, a FLASH-EPROM, a solid state medium like a memory card, any other memory chip or cartridge, or any other medium from which a computer can read. When the computer-readable media is configured as a database, it is to be understood that the database may be any type of database, such as relational, hierarchical, object-oriented, and/or the like. Accordingly, the invention is considered to include a tangible storage medium and prior art-recognized equivalents and successor media, in which the software implementations of the present invention are stored.

The terms "determine", "calculate" and "compute," and variations thereof, as used herein, are used interchangeably and include any type of methodology, process, mathematical operation or technique.

The term "module" as used herein refers to any known or later developed hardware, software, firmware, artificial intelligence, fuzzy logic, or combination of hardware and software that is capable of performing the functionality associated with that element. Also, while the invention is described in terms of exemplary embodiments, it should be appreciated that individual aspects of the invention can be separately claimed.

BRIEF DESCRIPTION OF THE DRAWINGS

The present disclosure is described in conjunction with the appended figures.

In the appended figures, similar components and/or features may have the same reference label. Further, various components of the same type may be distinguished by following the reference label by a letter that distinguishes among the similar components. If only the first reference label is used in the specification, the description is applicable to any one of the similar components having the same first reference label irrespective of the second reference label.

DETAILED DESCRIPTION

The ensuing description provides embodiments only, and is not intended to limit the scope, applicability, or configuration of the invention. Rather, the ensuing description will provide those skilled in the art with an enabling description for implementing the embodiments. It being understood that various changes may be made in the function and arrangement of elements without departing from the spirit and scope of the invention as set forth in the appended claims.

An embodiment of a system 100 operable to store customer information and provide products and/or services associated with the customer information. The system 100 includes a customer service server 110. The customer service server 110 can be any hardware and or software as described in conjunction with FIGS. 8 and 9. Generally, the customer service server 110 is a computer system operable to receive inputs about a customer from two or more sources, associated and consolidate the inputs, and store the inputs to a customer information database 112. The inputs can be any customer activity by a customer at any retail outlet associated with the business or organization. Customer activity can include information about purchases, searches performed on the Internet, in a store, by phone, etc., inquiries about financing options, inquiries about warranties, the number, location, duration, and other information about visits to retail locations (e.g. stores), the number, duration, and other information about visits to a website associated with the business, and other information. A retail outlet can be any retail location, Internet site, call center, or other entity or location where a customer can purchase or research products or services associated with the business or organization.

Figure 1:
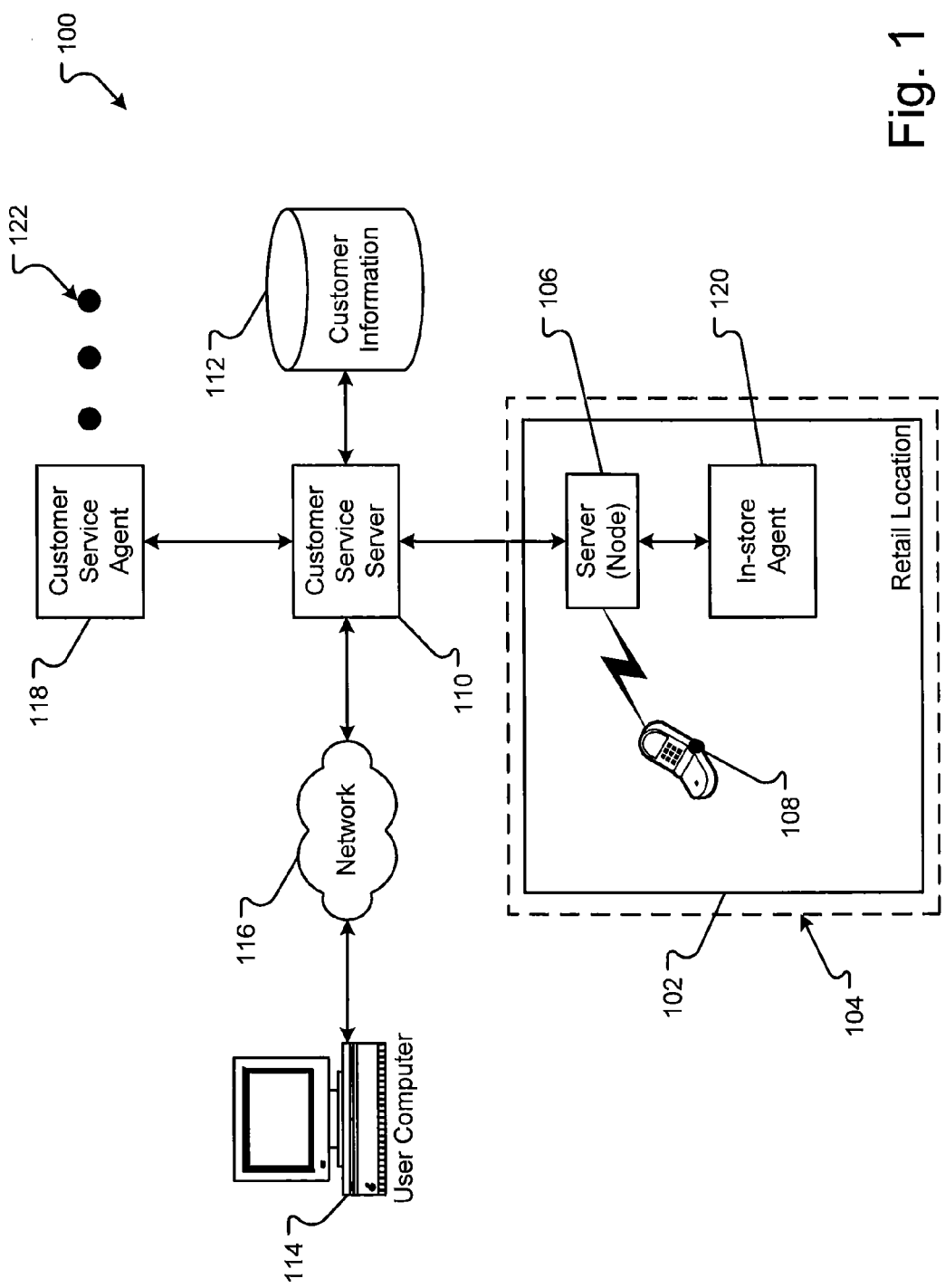
FIG. 1 is a block diagram of an embodiment of a system for interacting with customers and storing customer activity information.

Some of the possible interconnections with various retail outlets are shown in FIG. 1. In embodiments, a customer uses a user computer 114 to communicate with a website (not shown) through a network 116. The user computer 114 can be any computing system described in conjunction with FIGS. 8 and 9. Likewise, the network 116 can be any communication system or protocol as described in conjunction with FIGS. 8 and 9. Communications with the website may be monitored by the customer service server 110. If the user conducts a search, for example, searching for a product or service, the search requested, the results received, any product or service selected for further information, etc., can be monitored and stored to the customer information database 112.

In further embodiments, a customer service agent system 118 can communicate with the customer service server 110. A customer service agent system 118 can be a call center system that receives telephone calls or other customer contacts, e.g., email messages, instant messages, etc. Thus, the customer service agent system 118 can represent any computer system or network as described in conjunction with FIGS. 8 and 9 that enable the call center. Further, the customer service agent system 118 can include any computer system or network as described in conjunction with FIGS. 8 and 9 that may be part of a mail order processing system. The various types of systems that may embody a customer service agent system 118 are represented by the ellipses 122. The customer service agent system 118 communicates searches, inquiries, purchases, and other customer activity to the customer service server 110.

Further, the system 100 can include one or more retail locations 102. A retail location can be any physical store that allows a customer to view products or services, gather information about products or services, and/or order products or services. The retail location 102 can include a server or other computer system 106. The server 106 can be any computer system as described in conjunction with FIGS. 8 and 9. In alternative embodiments, the server 106 is replaced by a network node, e.g., a wireless access points or a physical network connection (such as an Ethernet cable that can be connected to a mobile device 108). The server 106 may communicate with mobile device 108. In other embodiments, the customer service server 110 communicates with the mobile device 108 through the node 106. Regardless, a system within the retail location 102 can communicate with a mobile device 108 associated with the customer. The mobile device 108 may be any computing system that is both portable and described in conjunction with FIGS. 8 and 9. For example, the mobile device 108 can be a cellular phone, a personal digital assistant, a laptop computer, a notebook computer, etc.

The retail location 102 may also be defined by a geo-fence 104 or it is possible to determine that the mobile device 108 is within perimeter 104. A geo-fence 104 is a perimeter substantially similar to the physical dimensions of the retail location 102 that allows a server or other computer system 106 to determine when a mobile device 108 associated with the customer is within or near the retail location 102. Geo-fencing or location determination is described in U.S. application Ser. No. 12/566,558, published, on Mar. 24, 2011, as U.S. Patent Application Publication 2011/0071889, having Avaya® Inc., entitled "Location-Aware Retail Application," U.S. application Ser. No. 12/240,256, published, on Apr. 1, 2010, as U.S. Patent Application Publication 2010/0079256, having Avaya® Inc., entitled "Monitoring Responsive Objects in Vehicles," and U.S. application Ser. No. 12/561,459, published, on Mar. 17, 2011, as U.S. Patent Application Publication 2011/ 0066423, having Avaya® Inc., entitled "'Speech-Recognition System for Location-Aware Applications," which are incorporated herein by reference in the documents' entirety for all that the applications teach. In embodiments, the server or node 106 communicates with the mobile device 108 when the mobile device 108 is determined to be within the geo-fence 104 or the retail location 102. The location of the mobile device 108 may be determined with GPS, geo-fencing, triangulation, through a presence system that determines and publishes the presence of the mobile device 108, or by other means.

The retail location 102 can also include an in-store agent computer system 120. The in-store agent computer system 120 also can be any computer system as described in conjunction with FIGS. 8 and 9. Similar to the customer service agent system 118, the in-store agent computer system 120 allows a sales agent or customer service agent at the retail location 102 to communicate information to the customer service server 110. The information communicated to the customer service server 110 can include searches, inquiries, purchases, and other customer activity.

The customer service server 110 can receive the various inputs from the retail outlets 118, 122, 114, 102, etc. In embodiments, the customer service server 110 is operable to associate the inputs from the retail outlets 118, 122, 114, and/or 102 to a customer. For example, the customer service server 110 can associate a username, password, customer name, mobile phone number, telephone number, or other biographical information that may be communicated from one or more of the various retail outlets 118, 122, 114, and/or 102. Thus, regardless of the retail outlet 118, 122, 114, and/or 102 that sends the input, the customer service server 110 can associate the input with the same customer and save the input to the customer's customer activity history.

In embodiments, the server or node 106 may push information to the mobile device 108. For example, the server or node 106 may push, to the mobile device 108, software applications or modifications to software applications already on the mobile device 108. The modifications can include new or additional features or functionality or a modification that enables or disables features on the mobile device 108. Thus, if the customer service server 110 determines from the customer activity or from a communication from the mobile device 108 that the user wants to test a software application, the server or node 106 can push the software application to the mobile device 108. In embodiments, the software application only functions while the mobile device 108 is inside or substantially near the geo-fence 104 or retail location 102. An embodiment of the server or node 106 that can push the software or other product or service to the mobile device 108 is shown in FIG. 2.

In embodiments, the server or node 106 may push information about product or service. Thus, the server or node 106 can determine or receive past customer activity from the customer service server 110. Then, the server or node 106 may relate the past customer activity with a physical location of the mobile device in the retail location 102. If the user is in an area of the retail location 102 displaying products or services associated with past customer activity, the server or node 106 can send information about the product or service associated with the customer activity to the mobile device 108. The information sent can be sales information, product information, etc.

In embodiments, the customer service server 110 can push a data element, such as a cookie, to the user computer 114. The cookie can stores at least a portion of the data in the customer information database 112 for the customer. The cookie can store the information for future retrieval. In some situations, the cookie can further store customer activity not related to the particular merchant but to other merchants. Thus, the cookie can store information about the customer's activity related to various related products that may be offered by different merchants or retailers. The cookie can contain at least a portion of a customer activity record that is described in conjunction with FIG. 4.

Figure 2:
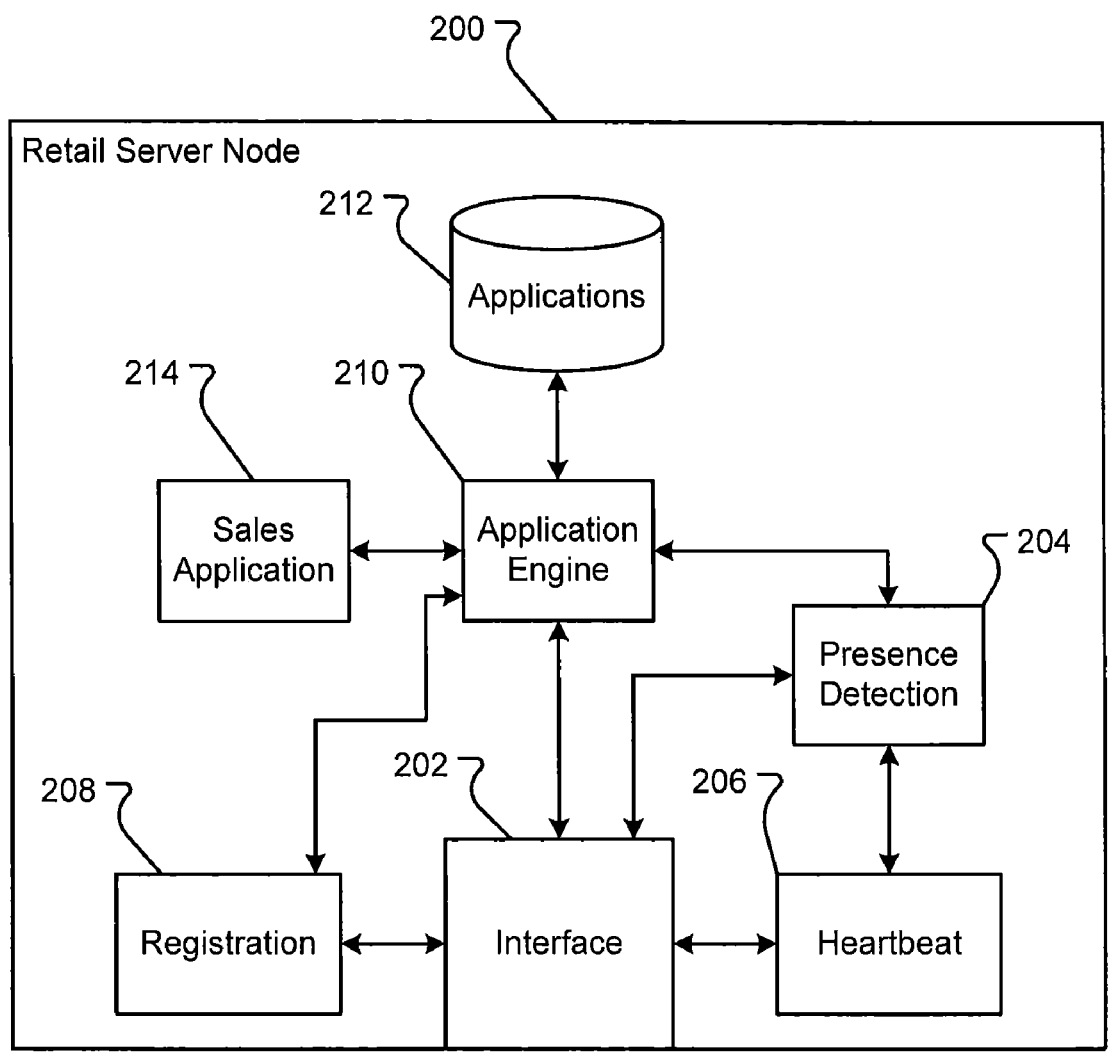
FIG. 2 is a block diagram of an embodiment of a retail server node.

The embodiment of the retail server node 200 shown in FIG. 2 may be the same or similar to server or node 106 shown in FIG. 1. The retail server node 200 can be a computer system as described in conjunction with FIGS. 8 and 9. Therefore, the components of the retail server node 200 may be software or computer executable instructions executed on a processor. However, in other embodiments, the components of the retail server node 200 may be specially designed hardware embodied in an application specific integrated circuit (ASIC), a field programmable gate array (FPGA), or other hardware device. Further, the components described in conjunction with FIG. 2 may also be a combination of hardware, software, firmware, etc.

The retail server node 200 can include an interface 202. The interface 202 can be any hardware or software to communicate with the mobile device 108 (FIG. 1). Example interfaces can include wireless access points communicating in 802.11g, 802.11N, Bluetooth™ Technology, or other wireless system. In other embodiments, the interface 202 can include a wired communication link, for example, an Ethernet or other connection to a local area network (LAN) in the retail location 102 (FIG. 1). The interface 202 is operable to receive data from or send data to the mobile device 108 (FIG. 1). In embodiments, the interface 202 can initiate a communication session by broadcasting the available connection to all mobile devices. The interface 202 can also receive a request to begin a communication session.

Upon making the initial connection to the interface, the mobile device 108 (FIG. 1) may be required to register with the retail server node 200 through the registration component 208. The registration component 208 communicates with the interface 202 to complete registration. The registration component 208 can request identifying information, for example, a username and password, a mobile device identifier, or other identifier. Registration may also require the user to install some application or establish an account with the retail server node 200. After registration, the registration component 208 can communicate with an application engine 210 the presence and registration of the mobile device 108 (FIG. 1). Presence may by the physical presence (defined by the physical location) of the mobile device or, in other embodiments, may mean the presence of the mobile device 108 as defined by a presence server or system. Further, the registration component 208 may communicate the registration information to the application engine 210 that can enable the application engine 210 to identify the customer associated with the mobile device 108 (FIG. 1).

In embodiments, a heartbeat component 206 can begin sending a heartbeat signal to the mobile device 108 (FIG. 1). A heartbeat signal can be any periodic signal that allows the retail server node 200 to determine if the mobile device 108 (FIG. 1) is still present in the retail location 102 (FIG. 1). In other embodiments, the heartbeat component 206 pushes an application to the mobile device 108 (FIG. 1) that causes the mobile device 108 (FIG. 1) to send the heartbeat signal to the retail server node 200. The heartbeat component 206 can then receive the heartbeat signal to determine that the mobile device 108 (FIG. 1) is still present in the retail location 102 (FIG. 1).

A presence detection component 204 can determine the continued presence of the mobile device 108 (FIG. 1). For example, the heartbeat component 206 can signal the presence detection component 204 that the heartbeat signal is being received. If the heartbeat signal stops, the heartbeat component 206 can signal the presence detection component 204. The presence detection component 204 may then communicate to the application engine 210 that the mobile device 108 (FIG. 1) is no longer present. In other embodiments, the presence detection component 204 determines that the mobile device 108 (FIG. 1) is present. For example, the presence detection component 204 may receive a location identifier (e.g., a Global Positioning System location, a triangulation location from three or more cellular towers, etc.) from the mobile device 108 (FIG. 1). The presence detection component 204 can compare this location identifier to the location of the retail location 102 (FIG. 1). If the locations compare, the presence detection component 204 informs the application engine 210 of the presence of the mobile device 108 (FIG. 1).

An application engine 210 is software operable to push applications to the mobile device 108 (FIG. 1). In embodiments, the application engine 210 begins a communication with the mobile device 108 (FIG. 1). The communication can be through an Internet page, an instant message, an email, a telephone call, or other communication being sent to the mobile device 108 (FIG. 1). The communication can be a request of whether the customer wants one or more applications to be pushed to the mobile device 108 (FIG. 1) for the customer to test. The application engine 210 can also send customer data and other information to the customer service server 110 (FIG. 1). With the customer data, the customer service server 110 (FIG. 1) may identify the customer and be able to store customer activity by the customer or push test applications to the retail server node 200 that the customer may be interested.

If the customer does want to test an application, the application engine 210 can retrieve the application from an application database 212. The application database 212 is any database application or hardware as described in conjunction with FIGS. 8 and 9. The application database 212 is operable to store one or more applications for the mobile device 108 (FIG. 1). A customer service server 110 (FIG. 1) can send the one or more applications to the retail server node 200 to store in the application database 212. Applications sent to the retail server node 200 by the customer service server 110 (FIG. 1) may depend on the identity of the customer.

If the customer determines that he or she wants to buy the test application, the mobile device 108 (FIG. 1) can send a signal requesting purchase to the application engine 210. The application engine 210 can then signal a sales application 214 of the customer's decision. The sales application 214 may then affect the purchase of the software. In other embodiments, the sales application alerts a sales agent or computer at the retail location 102 (FIG. 1) about the required purchase. Then, the purchase is made through the normal procedures in the retail location 102 (FIG. 1).

Figure 3:
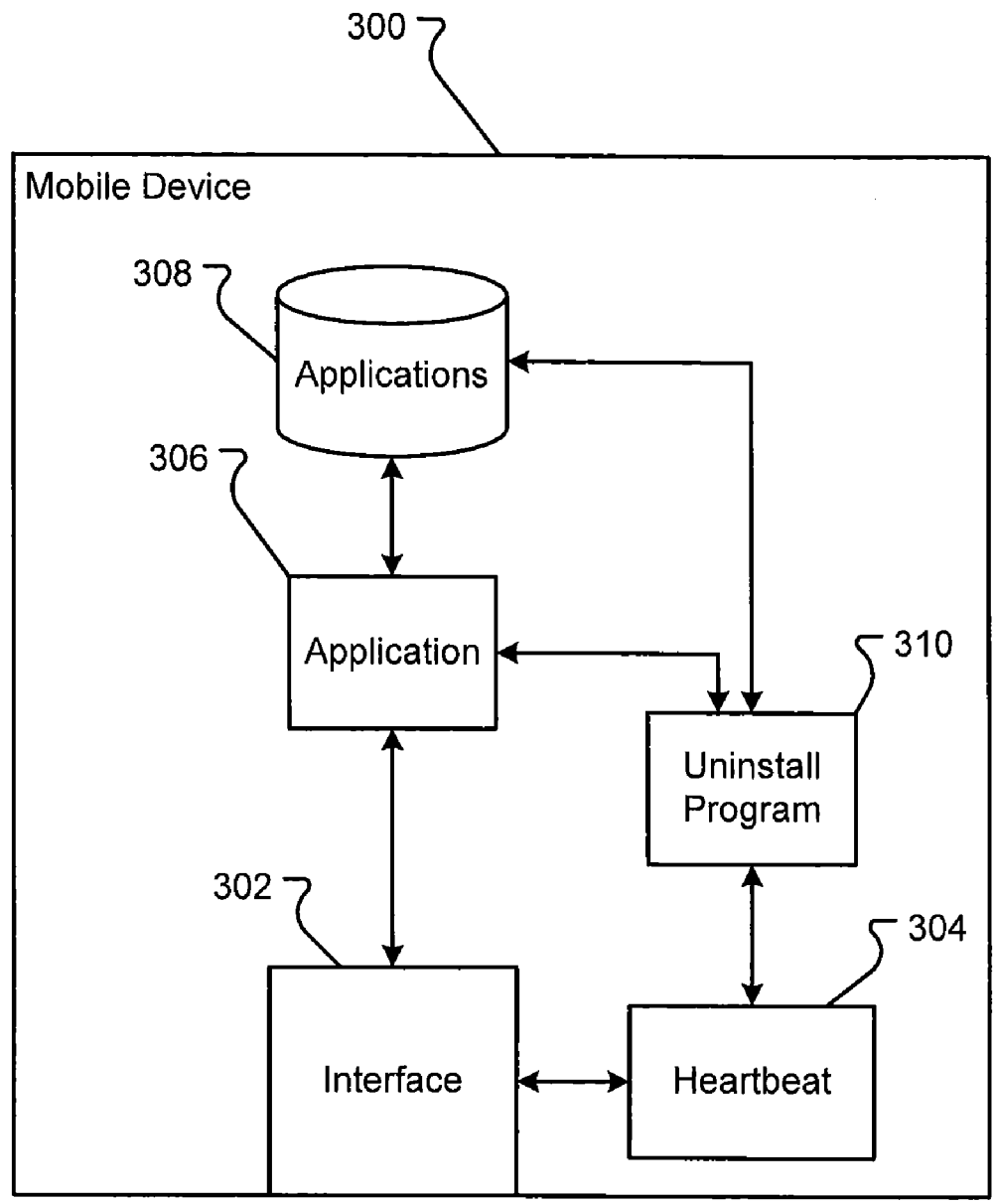
FIG. 3 is a block diagram of an embodiment of a mobile device.

An embodiment of a mobile device 300 is shown in FIG. 3. The mobile device 300 can be the same or similar to the mobile device 108 (FIG. 1). The mobile device 300 can be a computer system as described in conjunction with FIGS. 8 and 9. Therefore, the components of the mobile device 300 may be software or computer executable instructions executed on a processor. The mobile device 300 can include one or more other components not shown in FIG. 3. Indeed, the components explained in conjunction with FIG. 3 are associated with changes made to the mobile device 300 when interacting with the retail server node 200 (FIG. 2).

The mobile device 300 can include an interface 302. The interface 302 can be any hardware or software to communicate with the retail server node 200 (FIG. 2). Example interfaces can include wireless access points communicating in 802.11g, 802.11N, Bluetooth™ Technology, or other wireless systems. In other embodiments, the interface 302 can include a wired communication link, for example, an Ethernet or other connection to a local area network (LAN) in the retail location 102 (FIG. 1). The interface 302 is operable to receive data from or send data to the retail server node 200 (FIG. 2). In embodiments, the interface 302 can initiate a communication session by broadcasting the available connection to the mobile device (as with Bluetooth™ technology). The interface 302 can also receive a request to begin a communication session.

In embodiments, a heartbeat component 304 can receive a heartbeat application, install the heartbeat application, and begin sending a heartbeat signal to the retail server node 200 (FIG. 2). A heartbeat signal can be any periodic or other type of signal that shows the mobile device 300 is still present in the retail location 102 (FIG. 1). In other embodiments, the heartbeat application receives a heartbeat signal from the retail server node 200 (FIG. 2). Thus, the mobile device 300 determines if the mobile device 300 is still within the geofence 104 (FIG. 1) or the retail location 102 (FIG. 1). Again the heartbeat can be any signal that is received and can show the mobile device 300 is still present in the retail location 102 (FIG. 1).

An application 306 may be an application downloaded from the retail server node 200 (FIG. 2). An application 306 may be any process or software program executed to perform a function on the mobile device 300. The application 306 may be stored in an applications database 308, then executed by a processor on the mobile device 300. The applications database 308 can be any storage medium and/or database function as described in conjunction with FIGS. 8 and 9. In embodiments, the application 306 is selected by the user of the mobile device 300 and pushed to the mobile device in response to a request sent from the interface 302 to the retail server node 200 (FIG. 2).

In embodiments, the retail server node 200 (FIG. 2) also pushes an uninstall program 310 to the mobile device 300. The uninstall program 310 may be a software process or application that uninstalls the application 306 when the mobile device 300 leaves the geofence 104 (FIG. 1) or the retail location 102 (FIG. 1). Thus, the uninstall program 310 is an application that can erase the application 306 from the application database 308, can overwrite one or more portions of the application 306 to make the application unexecutable, or complete some action that prohibits the execution of the application 306. In embodiments, the uninstall program 310 is pushed to the mobile device 300 with the application 306, likely without the user's knowledge. After uninstall the application 306, the uninstall program 310 may also uninstall itself to eliminate most if not all of the download that was pushed to the mobile device. However, if the user purchases the application 306 through the retail sales node 200 (FIG. 2), the interface 302 may receive a signal acknowledging the purchase. The received signal can be sent to the uninstall program 310, which disables or erases the uninstall program 310, allowing the application 306 to execute even if the mobile device exits the geofence 104 (FIG. 1) or the retail location 102 (FIG. 1).

Figure 4:
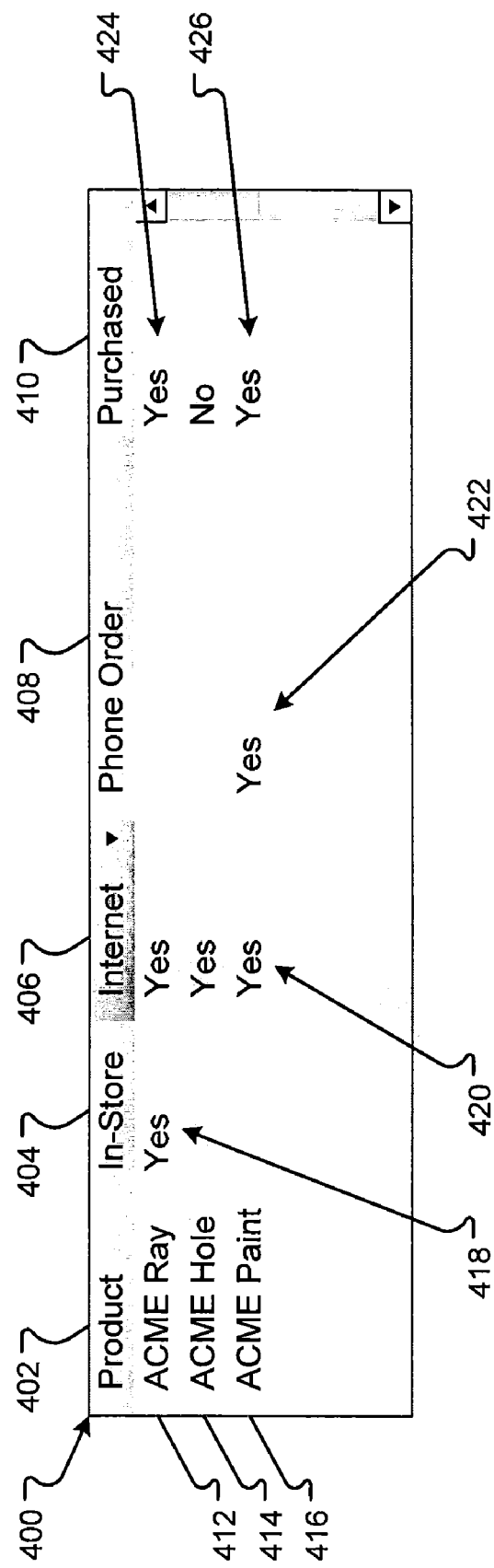
FIG. 4 is a block diagrams of an embodiment of a data structure that may be stored, sent, or received by one or more computer systems and represents a customer activity record.

An embodiment of a data structure 400 that can store customer activity is shown in FIG. 4. The data structure 400 can represent a customer activity record for a single customer. As such, there can be two or more customer activity records 400 for two or more customers stored in the customer information database 112 (FIG. 1), where each customer has a separate customer activity record 400. In embodiments, the customer activity record 400 includes one or more entries 412, 414, and/or 416 for each product and/or service investigated or purchased by a customer. For example, entry 412 stores the customer activity associated with the ACME Ray product, entry 414 stores the customer activity associated with the ACME Hole product, and entry 416 stores the customer activity associated with the ACME Paint service.

Each entry 412, 414, and/or 416 can include one or more fields. In embodiments, the entries 412, 414, and/or 416 include fields for the product and/or service 402, an indication of whether the customer researched the product in a store 404, an indication of whether the customer researched the product on an Internet website 406, an indication of whether the customer researched the product through a phone call to a customer service agent 408, and an indication of whether the customer purchased the product 410. Other fields not shown can include an indication of how the customer purchased the product (e.g., over the phone, from the Internet website, at a store), an identity for the store from which the customer purchased the product, the customer agent involved in providing information to the customer at the retail location, call center, or website, the customer agent involved in selling the product and/or service to the customer at the retail location, call center, or website, other retail outlets (e.g., mail order, outlet stores, third-party retailers, etc.), customer identity information, customer biographical information, and other information.

Exemplary data entries are included in the customer activity record 400. For example, this customer associated with the customer activity record 400 researched the ACME Ray product in entry 412 at a physical retail location (denoted by the "Yes" 418 in data field 404 for entry 412) and on an Internet website (denoted by the "Yes" in data field 406 for entry 412). The customer also purchased the ACME Ray product (denoted by the "Yes" 424 in data field 410 for entry 412). Similarly, this customer also researched the ACME Paint service in associated entry 416. The customer researched the ACME Paint service on an Internet website (denoted by the "Yes" 420 in data field 406 for entry 416) and over the phone to a customer service agent (denoted by the "Yes" 422 in data field 408 for entry 416). The customer also purchased this service (denoted by the "Yes" 426 in data field 410 for entry 416). In contrast, the customer researched the ACME Hole product associated with entry 414 but did not purchase the product (denoted by the "No" in data field 410 for entry 414).

Figure 5:
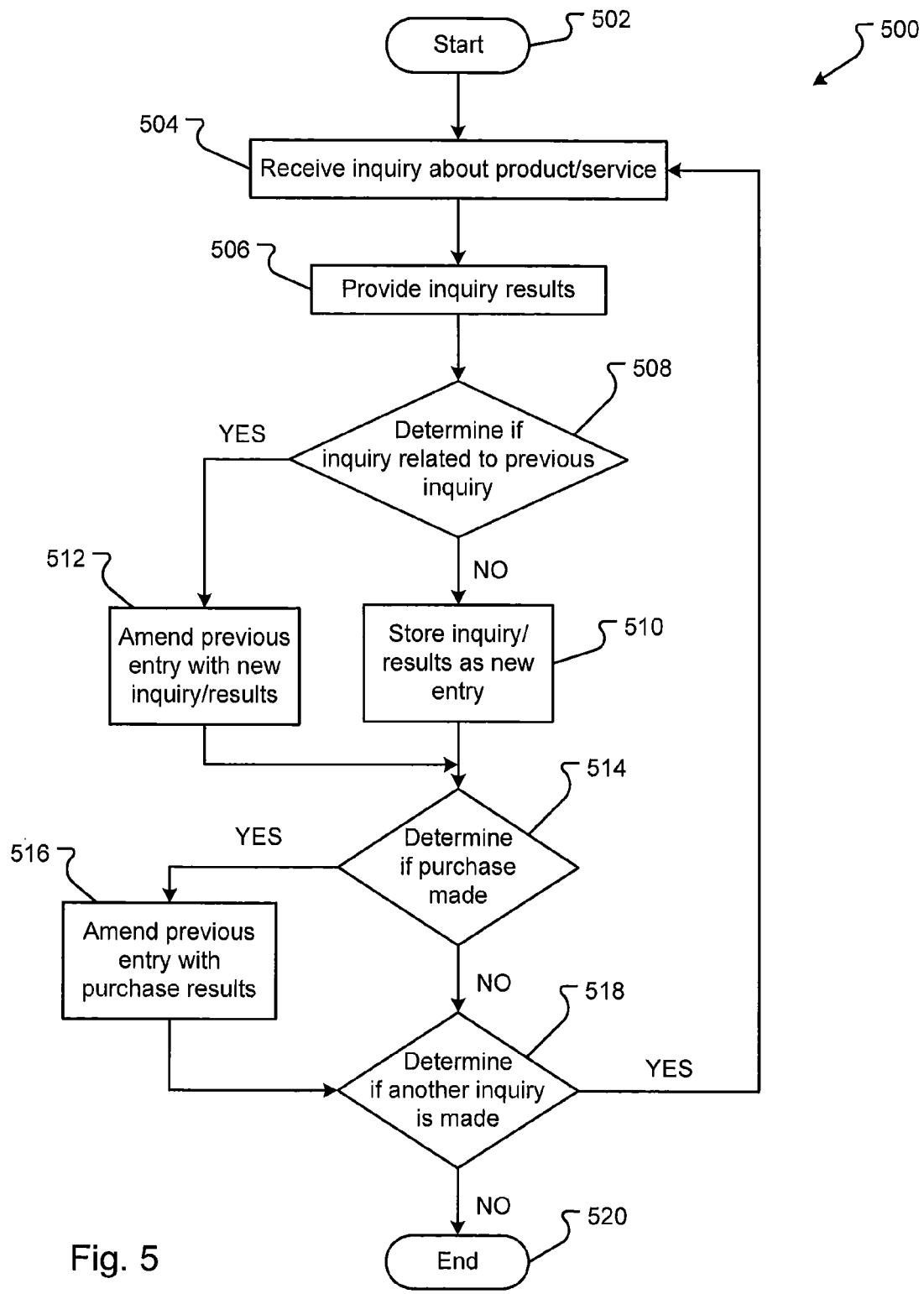
FIG. 5 is a flow diagram of an embodiment of a process for receiving and storing customer activity information.

An embodiment of a method 500 for collecting customer activity information is shown in FIG. 5. Generally, the method 500 begins with a start operation 502 and terminates with an end operation 520. While a general order for the steps of the method 500 are shown in FIG. 5, the method 500 can include more or fewer steps or arrange the order of the steps differently than those shown in FIG. 5. The method 500 can be executed as a set of computer-executable instructions executed by a computer system and encoded or stored on a computer readable medium. Hereinafter, the method 500 shall be explained with reference to the systems, components, modules, software, data structures, etc. described in conjunction with FIGS. 1-4.

The system 100 receives an inquiry about a product and/or service in step 504. The inquiry can be a request for information, a search for desired products or services, a purchase decision, a complaint, a letter of recommendation, or some other customer activity. The inquiry can be received by at least one interface with the customer. For example, the inquiry may be received by a customer service agent 118 operating in a call center or mail order processing center, by a website executing on the customer service server 110, by an in-store agent 120 at a retail location 102, by a third party vendor, or by some other entity or system in communication with the customer service server 112. The customer service server 110 can store the inquiry into a customer activity record 400 in the customer information database 112.

In response to the inquiry, the system 100 can provide results associated with the inquiry to the customer in step 506. The results can be any appropriate response to the inquiry including a provision of information, a provision of search results, a purchase completion and provision of the product or service, response to a complaint, response to a letter of recommendation, or some other response to the customer activity. In embodiments, the customer service server 110 can provide the response through an interface, for example, the customer service agent 118 operating in a call center or mail order processing center, the website executing on the customer service server 110, the in-store agent 120 at a retail location 102, a third party vendor, or by some other entity or system in communication with the customer service server 112. In other embodiments, the response is provided directly by one or more interfaces described above. The customer service server 110 may store the results from the inquiry into a customer activity record 400 in the customer information database 112.

To store either the indication of an inquiry or the content of the inquiry and the results of the inquiry, the customer service server 110 determines if the inquiry is related to a previous inquiry in step 508. The customer service server 110 searches the customer activity records 400 stored in the customer information database 112. A customer identity (e.g., a customer name, a credit card number, a loyalty program identifier, etc.) and a product or service identifier (e.g., a stock-keeping unit (SKU) code, a product or service number, may be provided during the inquiry. The customer identity can be used to locate the customer activity record 400 associated with the customer. Then, the customer service server 110 can search the located customer activity record 400 to determine if the product or service is listed in the product data field 402. If the product or service is listed in the product data field 402, the method 500 flows YES to step 512. If the product or service is not listed in the product data field 402, the method 500 flows NO to step 510.

In step 512, the customer service server 110 adds the customer activity to the customer activity record 400. For example, if the customer activity is a search inquiry for the ACME Hole on the Internet, the customer service server 110 stores a YES in the Internet data field 406 for entry 414. If there is no entry field for the product or service or customer activity record for the user, the customer service server 110 creates and stores the inquiry information as a new entry in step 510. Thus, the customer service server 110 can create a customer activity record 400 or a new entry in an existing customer activity record 400. The information is then stored in the entry. For example, the name of the service ACME Paint is placed in the product name field 402 and stores a YES in the Internet data field 406 for entry 416. As such, the customer service server 110 tracks all customer activity related to a product or service in which a customer may be interested. This tracking information allows the organization to determine customer behaviour and determine the interrelationships between inquiries on the phone, website, mail order processing, and retail stores.

Further, the customer service server 110 can determine if a purchase was made for a product associated with an inquiry in step 514. The customer service server 110 can receive sales information from a customer activity interface if a product or service is sold. If purchase information is received, the customer service server 110 determines a purchase has been made and the method 500 flows YES to step 516. If no purchase is made, the method 500 flows NO to step 518. In step 516, the customer service server 110 adds the purchase activity information to the customer activity record 400. For example, if the purchase is for the ACME Ray, the customer service server 110 stores a YES in the purchase field 424 for entry 412. The changed customer activity record 400 can be stored in the customer information database 112 or as a cookie or data element on the user computer 114.

The customer service server 110 can then determine if there is another inquiry in step 518. The customer service server 110 wait for another inquiry from the same or different customer. If another inquiry is received, the method 500 flows YES back to step 504. If not other inquiry has been made, the method 500 flows NO to end 520, which may entail the customer service server 110 waiting for another inquiry at a later time or date. In this way, the system 100 tracks customer activity across all organizational interfaces (retail outlets) where the customer activity is more than simple purchase decisions.

Figure 6:
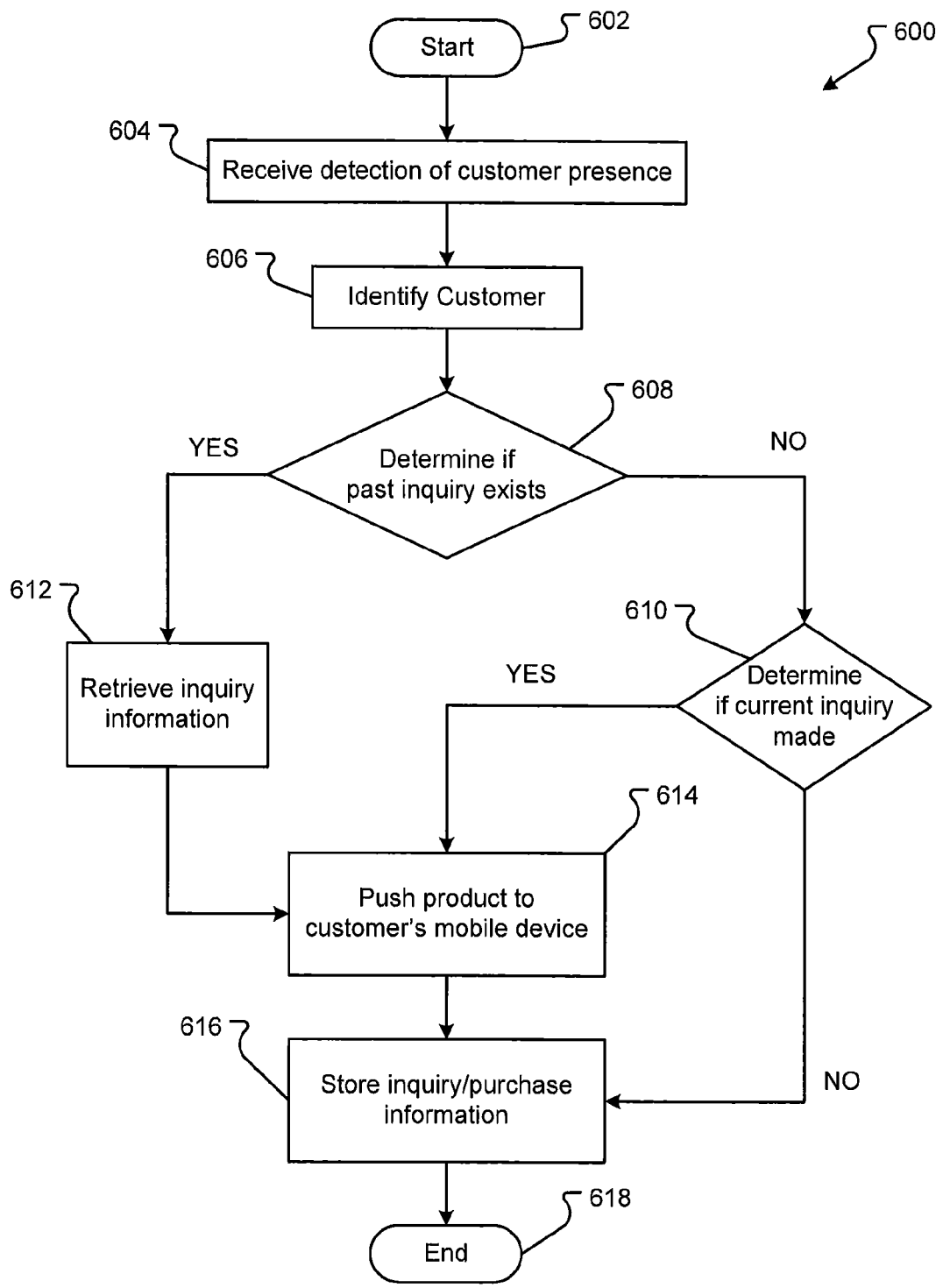
FIG. 6 is a flow diagram of an embodiment of a process for determining available products, based on past customer activity, to provide to the customer for testing.

An embodiment of a method 600 for providing a customer with a demonstration product associated with an inquiry is shown in FIG. 6. Generally, the method 600 begins with a start operation 602 and terminates with an end operation 618. While a general order for the steps of the method 600 are shown in FIG. 6, the method 600 can include more or fewer steps or arrange the order of the steps differently than those shown in FIG. 6. The method 600 can be executed as a set of computer-executable instructions executed by a computer system and encoded or stored on a computer readable medium. Hereinafter, the method 600 shall be explained with reference to the systems, components, modules, software, data structures, etc. described in conjunction with FIGS. 1-4.

A retail server node 106 can receive the detection of the presence of a customer in a retail location 102 in step 604. In embodiments, a mobile device 108 associated with the customer signals the presence of the mobile device 108 within the retail location 102. For example, the mobile device 108 may broadcast a request for a Bluetooth™ connection or may start a handshake sequence after being physically connected to an inter-store network. In other embodiments, the retail server node 106 sends a signal to start a communication and receives a reply as a signal of the presence of the mobile device 108.

The retail server node 106 may then determine the identity of the customer in step 606. To identify the customer, a registration component 208 of the retail server node 200 can send a registration request from the interface 202 to the interface 302 of the mobile device 300. The registration request can include a request for one or more items of information to be input by a user of the mobile device 200. The user may respond to the request by inputting the information on the user interface of the mobile device 200. Information associated with the registration is then sent by the interface 302 to the interface 202 of the retail server node 200. The information may then be sent to the registration component 214 from the interface 202. A customer identity may be determined from the registration information. For example, if a user enters a name or other identifier, the retail server node 200 can forward that information to the customer service server 110. The customer service server 110 can then search the customer information database 112 for the user identity. In embodiments, the retail server node 200 also sends an indication of the registration to the application engine 210.

The customer may then begin shopping. In embodiments, the customer may inquire about a product. A product identifier for the product may also be sent by the retail server node 200 to the customer service server 110. Regardless, the customer service server 110 may determine if the customer has made any past inquiries into the product with the product identifier or inquiries into any products or services in step 608. The customer service server 110 can search the customer information database 112 for a customer activity record 400 associated with the customer. In other words, the customer service server 110 determines if a customer activity record 400 includes the customer's identity information. If a customer activity record 400 does include the customer identity, the customer service server 110 can search for an entry 412, 414, or 416 about one or more products or services. If an entry 412, 414, or 416 does exist, the method 600 flows YES to step 612. If a customer activity record 400 or an entry 412, 414, or 416 does not exist, the method 600 flows NO to step 610.

In step 612, the customer service server 110 retrieves the inquiry information from the customer activity record 400. For example, the customer service server 110 may retrieve the products 402 inquired by the customer in the entries 412, 414, or 416. Further, the customer service server 110 may eliminate any information related to an inquiry that is associated with a purchase in data field 410. Thus, the information can include only products or services that the customer is interested but has not yet purchased.

The retail server node 200 or the customer service server 110 may determine if the customer is making a current inquiry. In embodiments, the retail server node 200 or the customer service server 110 may send a message to the mobile device 300. The message may be a request whether the customer is interested in one or more products (e.g., software applications for the mobile device 300). The interface 302 can receive the request and display the request on the mobile device user interface. In other embodiments, the sales agent may send information from the in-store agent computer 120 to the retail server node 200 or the customer service server 110 that details the products or services being asked about in the retail location 102. Regardless, if a current inquiry is being made, the method 600 flows YES to step 614. If a current inquiry is being made, the method 600 flows YES to step 614. If no current inquiry is being made, the method 600 flows NO to step 616.

The retail server node 200 can push a product to the mobile device 108 in step 614. Thus, if the user made an inquiry in the past or is making a current inquiry about a product, the retail server node 200 can push that product to the mobile device 108. Generally, the product is a software application that can be executed on the customer's mobile device 108. In this way, a customer can test the application in the same environment that the application will be used, namely, the mobile device 108 which will execute the application. The software application may also be sent from the customer service server 110 to the retail server node 200 and then to the mobile device 108. An embodiment of a method for pushing the product to the mobile device 108 is described in conjunction with FIGS. 7A and 7B.

The retail server node 200 may send any information collected about the interaction with the customer to the customer service server 110. The customer service server 110 may then store any inquiry or purchase information into the customer information database 112 in step 616. The customer service server 110 can create or collect the customer activity record 400 and enter new information into the customer activity record 400. The information entered can include placing a "Yes" into the data field 404 for a new or amended entry 412, 414, or 416. Further, the information can include storing a "Yes" in the data field 410 if the customer purchased a product.

Figure 7A:
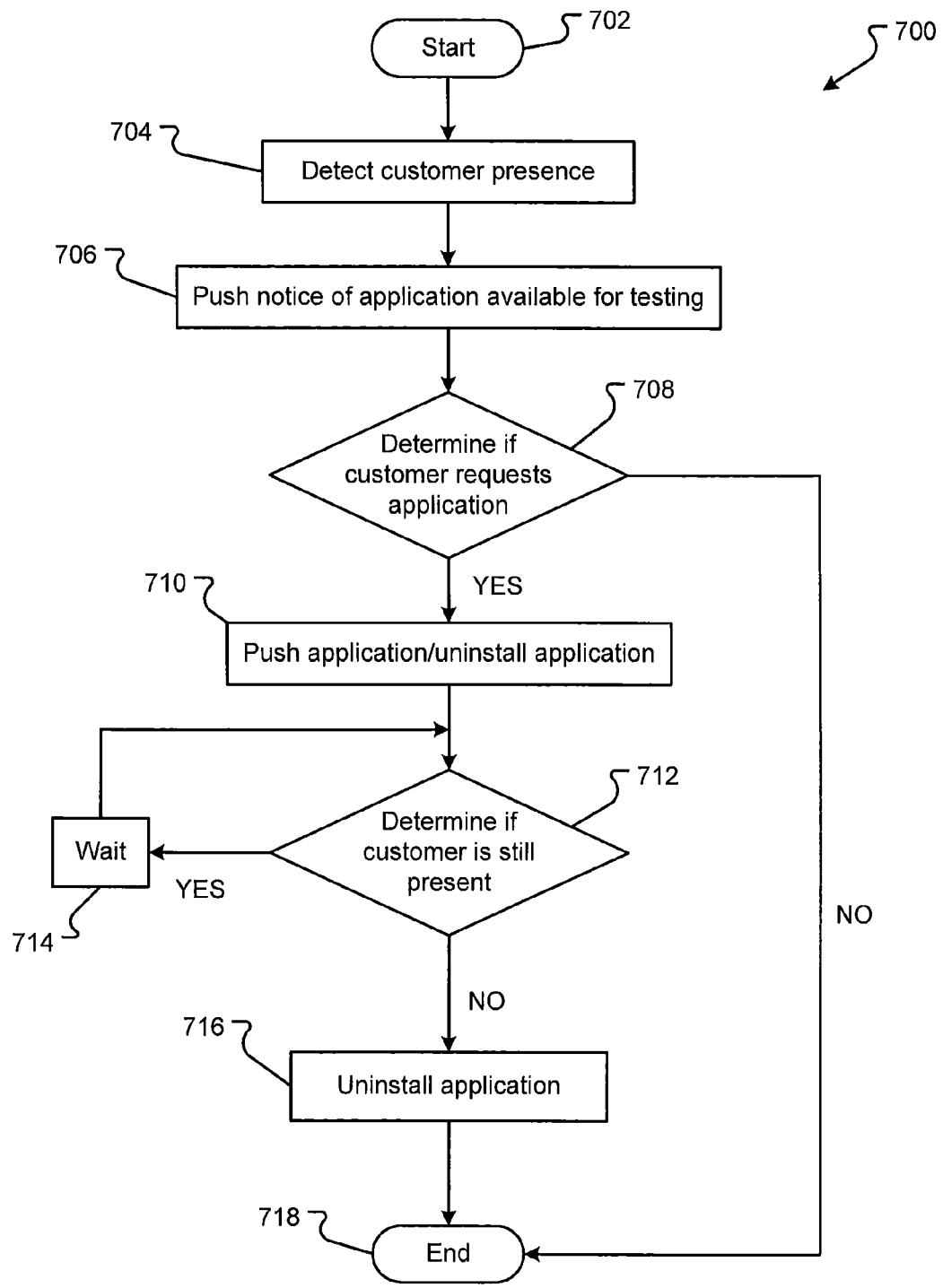
FIGS. 7A and 7B are flow diagrams of embodiments of processes for pushing a test software application to a customer's mobile device.
Figure 7B:
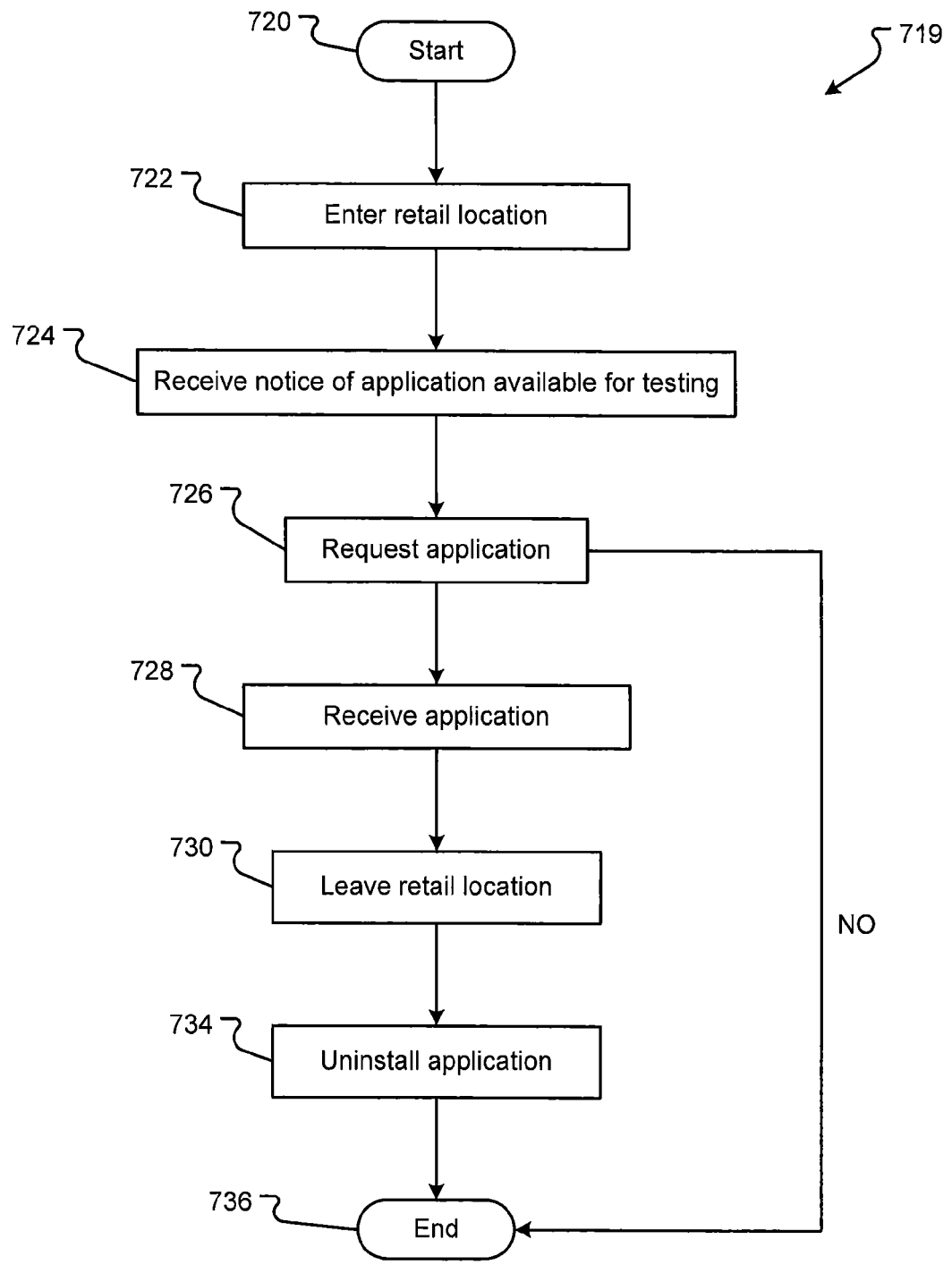

An embodiment of a method 700 for pushing a product, such as a software application, to a customer's mobile device is shown in FIGS. 7A and 7B. FIG. 7A describes the process 700 from the perspective of the retail server node 200, while FIG. 7B described the process 719 from the perspective of the mobile device 200. Generally, the methods 700 and 719 begin with a start operation 702 and 720, respectively, and terminate with an end operation 718 and 736, respectively. While a general order for the steps of the methods 700 and 719 are shown in FIGS. 7A and 7B, the method 700 can include more or fewer steps or arrange the order of the steps differently than those shown in FIGS. 7A and 7B. The methods 700 and 719 can be executed as a set of computer-executable instructions executed by a computer system and encoded or stored on a computer readable medium. Hereinafter, the methods 700 and 719 shall be explained with reference to the systems, components, modules, software, data structures, etc. described in conjunction with FIGS. 1-4.

A customer, with a mobile device 108, can enter a retail location 102 in step 722. After the customer enters the geofenced area 104, the retail server node 200 may detect the presence of the mobile device 108 in step 704. Determining the presence of, registering, and otherwise interacting with the mobile device 108 may be as explained in conjunction with FIG. 6. The retail server node 200 can then push a notice of a software application that may be available for testing in step 706. The notice can be a web page or other displayable alert that the customer may see on the user interface of the mobile device 108. In embodiments, the application engine 210 of the retail server node 200 generates the notice and sends the notice to the interface 202 to send to the mobile device 108. The mobile device 108 receives the notice of the available software application in step 724. The interface 302 can receive the notice and send the notice to the processor to render. The mobile device 108 may then display the notice to the customer on the user interface.

If the customer desires to test the software application, the customer can select a user interface device to request the application. If the customer requests the application, the mobile device 108 may respond to the notice by sending a request for the application in step 726 from the interface 302. The interface 202 of the retail server node 200 can receive the request for the application and send the request to the application engine 210. The application engine 210 may determine if the customer requests the application in step 708. If the application engine 210 receives the request, the application engine 210 can determine that the customer requests the application. The method 700 then flows YES to step 710. If the application engine 210 waits a predetermined amount of time and no request is received, the application engine 210 can determine that the customer does not request the application. Then, the method 700 flows NO to step 718. In other embodiments, the method 700 may flow NO to step 706 where the retail server node 106 pushes a new notice of a different application to the customer's mobile device 108.

In step 710, the application engine 210 creates a package to send to the mobile device 300. The package includes the application retrieved from the applications database 212 and an uninstall application. The package is sent to the interface 202, which sends the package to the mobile device 300. The interface 302 of the mobile device 300 receives both the application and the uninstall application in step 728. The processor of the mobile device 300 can store the application in the applications database 308 and install and execute the application 306. Further, the processor install and executes the uninstall program 310. The presence and execution of the uninstall program 310 may be unknown to the customer. The mobile device 300 continues to execute the application.

While the mobile device 300 executes the application, the retail server node 200 determines if the customer is still present in the retail location 102 in step 712. In embodiments, the retail server node 200 determines if the mobile device 108 is still within the geofence 104. In other embodiments, the retail server node 200 receives a heartbeat signal from a heartbeat application 304, which was also installed with the application 306. If the heartbeat is still present, the mobile device 108 remains within the retail location 102. If the mobile device 108 is still within the retail location 102, the method 700 flows YES to step 714 where the retail server node 200 waits a predetermined period of time before determining if the mobile device 108 is still present in step 712. If the customer leaves the retail location in step 730, the method 700 flows NO to step 716.

One or both of the retail server node 200 and the mobile device 300 may be involved in uninstalling the application in step 716 and step 734. In embodiments, if the heartbeat application 206 no longer receives the heartbeat signal from the mobile device 300, the heartbeat application 206 sends a signal to the presence detection component 204 indicating the mobile device 300 is no longer located in the retail location 102. The presence detection component 204 alerts the application engine 210 of the change in presence status. In response to the change in status, the application engine 210 sends an uninstall signal to the interface 202, which sends the uninstall signal to the mobile device 300. In response to receiving the uninstall signal, the uninstall application 310 uninstalls the application 306, deletes the application from the applications database 308, and/or makes the application 306 unusable by known means.

In other embodiments, the heartbeat application 206 of the retail server node 200 sends a heartbeat signal to the heartbeat application 304 of the mobile device 300. When the customer leaves the retail location 104, the heartbeat signal dissipates and is no longer received. In response to losing the heartbeat signal, the heartbeat application 304 can alert the uninstall program 310 of the change in presence status. In response to the change in status, the uninstall program 310 uninstalls the application 306, deletes the application from the applications database 308, and/or makes the application 306 unusable by known means. Further, either the retail server node 200 or the mobile device 300 may wait a predetermined period of time after losing the heartbeat signal to begin the uninstall procedure. In this way, if the customer briefly loses the heartbeat signal or quickly leaves and reenters the store (such as to flag a friend or relative), the uninstall procedure will not be invoked. This predetermined period of time to wait can be counted by the processor after losing the heartbeat signal.

Figure 8:
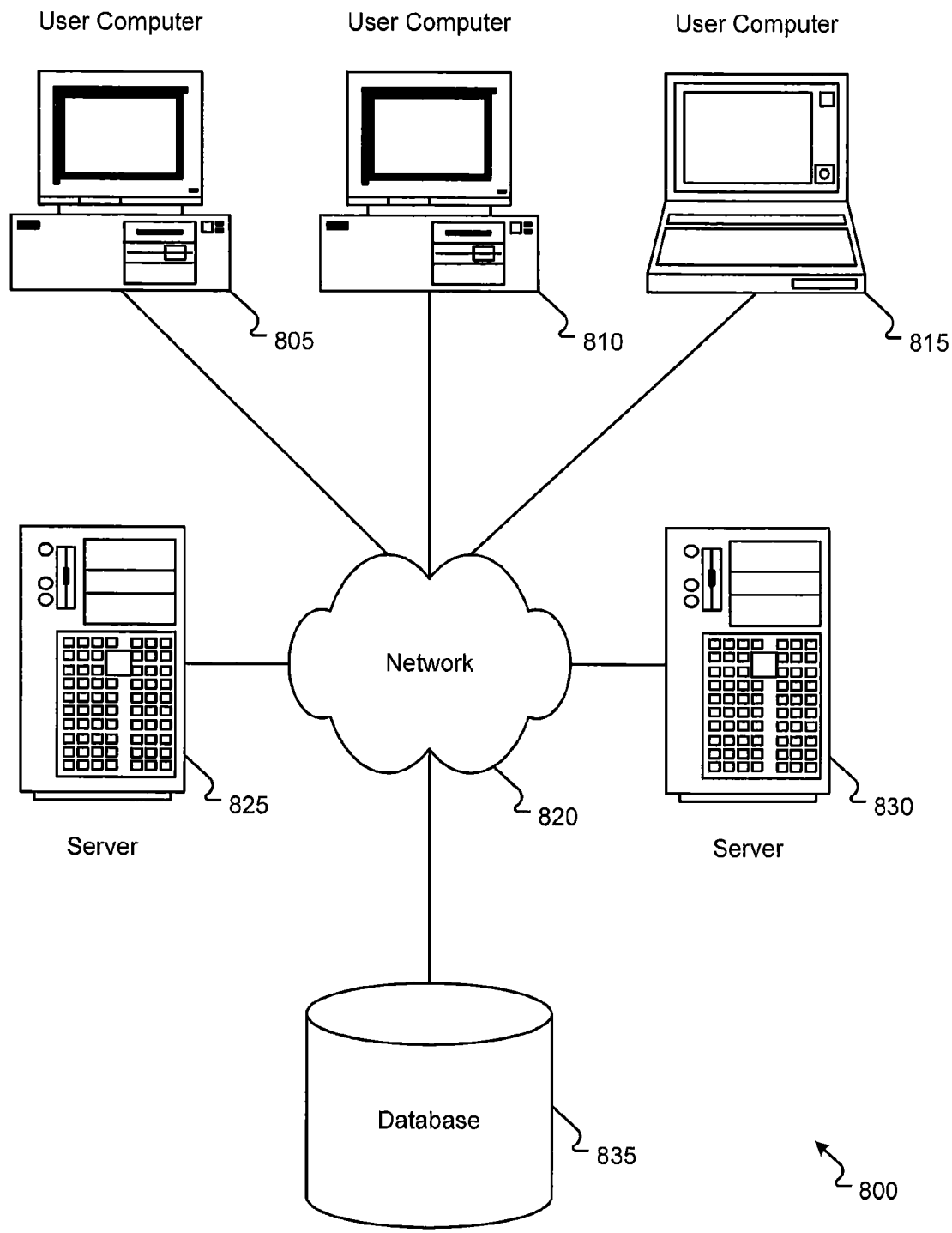
FIG. 8 is a block diagram of an embodiment of a computer system environment in which the systems and methods may be executed.

FIG. 8 illustrates a block diagram of a computing environment 800 that may include the mobile device 108, the retail server node 106, the customer service server 110, the user computer 114, the in-store agent computer 120, the customer service agent computer 118, or other system described herein. The system 800 includes one or more computers 805, 810, and 815. The computers 805, 810, and 815 may be general purpose personal computers (including, merely by way of example, personal computers and/or laptop computers running various versions of Microsoft Corp.'s Windows® and/or Apple Corp.'s Macintosh® operating systems) and/or workstation computers running any of a variety of commercially-available UNIX® or UNIX-like operating systems. These computers 805, 810, 815 may also have any of a variety of applications, including for example, database client and/or server applications, and web browser applications. Alternatively, the computers 805, 810, and 815 may be any other electronic device, such as a thin-client computer, mobile telephone, mobile device, Internet-enabled mobile telephone, and/or personal digital assistant, capable of communicating via a network (e.g., the network 820 described below) and/or displaying and navigating web pages or other types of electronic data. Although the exemplary system 800 is shown with three computers, any number of computers may be supported.

System 800 further includes a network 820. The network 820 may can be any type of network familiar to those skilled in the art that can support data communications using any of a variety of commercially-available protocols, including without limitation TCP/IP, SNA, IPX, AppleTalk, and the like. Merely by way of example, the network 820 maybe a local area network ("LAN"), such as an Ethernet network, a Token-Ring network and/or the like; a wide-area network; a virtual network, including without limitation a virtual private network ("VPN"); the Internet; an intranet; an extranet; a public switched telephone network ("PSTN"); an infra-red network; a wireless network (e.g., a network operating under any of the IEEE 802.11 suite of protocols, the Bluetooth® protocol known in the art, and/or any other wireless protocol); and/or any combination of these and/or other networks. The network 820 may be the same or similar to network 116 or other networks allowing communication between the various systems and components described herein.

The system 800 may also include one or more server computers 825 and 830. The server computers 825 and/or 830 can represent any of the retail server node 106, the customer service server 110, the user computer 114, the in-store agent computer 120, the customer service agent computer 118, or other system described herein. One server may be a web server 825, which may be used to process requests for web pages or other electronic documents from user computers 805, 810, and 820. The web server can be running an operating system including any of those discussed above, as well as any commercially-available server operating systems. The web server 825 can also run a variety of server applications, including HTTP servers, FTP servers, CGI servers, database servers, Java servers, and the like. In some instances, the web server 825 may publish operations available operations as one or more web services.

The system 800 may also include one or more file and or/application servers 830, which can, in addition to an operating system, include one or more applications accessible by a client running on one or more of the user computers 805, 810, 815. The server(s) 830 may be one or more general purpose computers capable of executing programs or scripts in response to the user computers 805, 810 and 815. As one example, the server may execute one or more web applications. The web application may be implemented as one or more scripts or programs written in any programming language, such as Java™, C, C#™ or C++, and/or any scripting language, such as Perl, Python, or TCL, as well as combinations of any programming/scripting languages. The application server(s) 830 may also include database servers, including without limitation those commercially available from Oracle, Microsoft, Sybase™, IBM™ and the like, which can process requests from database clients running on a user computer 805.

The web pages created by the web application server 830 may be forwarded to a user computer 805 via a web server 825. Similarly, the web server 825 may be able to receive web page requests, web services invocations, and/or input data from a user computer 805 and can forward the web page requests and/or input data to the web application server 830. In further embodiments, the server 830 may function as a file server. Although, for ease of description, FIG. 8 illustrates a separate web server 825 and file/application server 830, those skilled in the art will recognize that the functions described with respect to servers 825, 830 may be performed by a single server and/or a plurality of specialized servers, depending on implementation-specific needs and parameters.

The system 800 may also include a database 835, which may be the same or similar to database 112, 212, and/or 308. The database 835 may reside in a variety of locations. By way of example, database 835 may reside on a storage medium local to (and/or resident in) one or more of the computers 805, 810, 815, 825, 830. Alternatively, it may be remote from any or all of the computers 805, 810, 815, 825, 830, and in communication (e.g., via the network 820) with one or more of these. In a particular set of embodiments, the database 835 may reside in a storage-area network ("SAN") familiar to those skilled in the art. Similarly, any necessary files for performing the functions attributed to the computers 805, 810, 815, 825, 830 may be stored locally on the respective computer and/or remotely, as appropriate. In one set of embodiments, the database 835 may be a relational database, such as Oracle 10i®, that is adapted to store, update, and retrieve data in response to SQL-formatted commands. The database 835 may be operable to store data structure 400.

Figure 9:
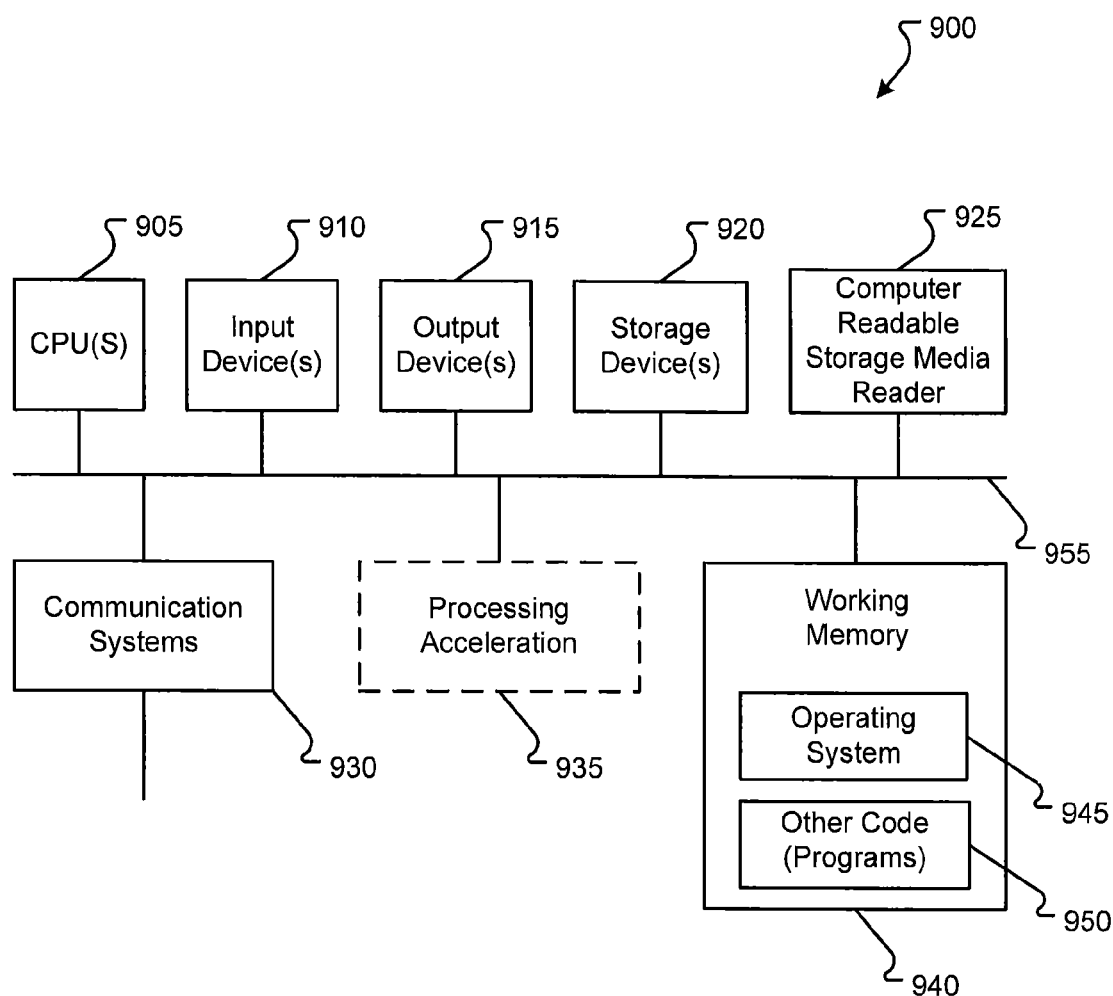
FIG. 9 is a block diagram of a computer system in which the systems and methods may be executed.

FIG. 9 illustrates one embodiment of a computer system 900 upon which mobile device 108, the retail server node 106, the customer service server 110, the user computer 114, the in-store agent computer 120, the customer service agent computer 118, or other systems described herein may be deployed or executed. The computer system 900 is shown comprising hardware elements that may be electrically coupled via a bus 955. The hardware elements may include one or more central processing units (CPUs) 905; one or more input devices 910 (e.g., a mouse, a keyboard, etc.); and one or more output devices 915 (e.g., a display device, a printer, etc.). The computer system 900 may also include one or more storage devices 920. By way of example, storage device(s) 920 may be disk drives, optical storage devices, solid-state storage devices, such as a random access memory ("RAM") and/or a read-only memory ("ROM"), which can be programmable, flash-updateable, and/or the like.

The computer system 900 may additionally include a computer-readable storage media reader 925; a communications system 930 (e.g., a modem, a network card (wireless or wired), an infra-red communication device, etc.); and working memory 940, which may include RAM and ROM devices as described above. In some embodiments, the computer system 900 may also include a processing acceleration unit 935, which can include a DSP, a special-purpose processor and/or the like The computer-readable storage media reader 925 can further be connected to a computer-readable storage medium, together (and, optionally, in combination with storage device(s) 920) comprehensively representing remote, local, fixed, and/or removable storage devices plus storage media for temporarily and/or more permanently containing computer-readable information. The communications system 930 may permit data to be exchanged with the network 920 and/or any other computer described above with respect to the system 900. Moreover, as disclosed herein, the term "storage medium" may represent one or more devices for storing data, including read only memory (ROM), random access memory (RAM), magnetic, RAM, core memory, magnetic disk storage mediums, optical storage mediums, flash memory devices, and/or other machine readable mediums for storing information.

The computer system 900 may also comprise software elements, shown as being currently located within a working memory 940, including an operating system 945 and/or other code 950, such as program code implementing the components and software described herein. It should be appreciated that alternate embodiments of a computer system 900 may have numerous variations from that described above. For example, customized hardware might also be used and/or particular elements might be implemented in hardware, software (including portable software, such as applets), or both.

Further, connection to other computing devices such as network input/output devices may be employed.

In the foregoing description, for the purposes of illustration, methods were described in a particular order. It should be appreciated that in alternate embodiments, the methods may be performed in a different order than that described. It should also be appreciated that the methods described above may be performed by hardware components or may be embodied in sequences of machine-executable instructions, which may be used to cause a machine, such as a general-purpose or special-purpose processor or logic circuits programmed with the instructions to perform the methods. These machine-executable instructions may be stored on one or more machine readable mediums, such as CD-ROMs or other types of optical disks, floppy diskettes, ROMs, RAMs, EPROMs, EEPROMs, magnetic or optical cards, flash memory, or other types of machine-readable mediums suitable for storing electronic instructions. Alternatively, the methods may be performed by a combination of hardware and software.

Specific details were given in the description to provide a thorough understanding of the embodiments. However, it will be understood by one of ordinary skill in the art that the embodiments may be practiced without these specific details. For example, circuits may be shown in block diagrams in order not to obscure the embodiments in unnecessary detail. In other instances, well-known circuits, processes, algorithms, structures, and techniques may be shown without unnecessary detail in order to avoid obscuring the embodiments.

Also, it is noted that the embodiments were described as a process which is depicted as a flowchart, a flow diagram, a data flow diagram, a structure diagram, or a block diagram. Although a flowchart may describe the operations as a sequential process, many of the operations can be performed in parallel or concurrently. In addition, the order of the operations may be re-arranged. A process is terminated when its operations are completed, but could have additional steps not included in the figure. A process may correspond to a method, a function, a procedure, a subroutine, a subprogram, etc. When a process corresponds to a function, its termination corresponds to a return of the function to the calling function or the main function.

Furthermore, embodiments may be implemented by hardware, software, firmware, middleware, microcode, hardware description languages, or any combination thereof. When implemented in software, firmware, middleware or microcode, the program code or code segments to perform the necessary tasks may be stored in a machine readable medium such as storage medium. A processor(s) may perform the necessary tasks. A code segment may represent a procedure, a function, a subprogram, a program, a routine, a subroutine, a module, a software package, a class, or any combination of instructions, data structures, or program statements. A code segment may be coupled to another code segment or a hardware circuit by passing and/or receiving information, data, arguments, parameters, or memory contents. Information, arguments, parameters, data, etc. may be passed, forwarded, or transmitted via any suitable means including memory sharing, message passing, token passing, network transmission, etc.

While illustrative embodiments of the invention have been described in detail herein, it is to be understood that the inventive concepts may be otherwise variously embodied and employed, and that the appended claims are intended to be construed to include such variations, except as limited by the prior art.

What is claimed is:

1. A method for providing a product to a customer for a limited time, the method comprising:
    a retail server node receiving a detection of a presence of the customer in a geo-fenced, physical retail location based on a Global Positioning System ("GPS") location;
    the retail server node identifying the customer;
    the retail server node determining if the customer made a past inquiry about a product the customer has yet to purchase;
    if the customer made a past inquiry about a product the customer has yet to purchase, the retail server node retrieving inquiry information for the past inquiry;
    based on the retrieved inquiry information, the retail server node pushing the unpurchased product to a mobile device of the customer to test while the customer is in the geo-fenced, physical retail location;
    the retail server node allowing the customer to test the product on the mobile device while the customer remains in the geo-fenced, physical retail location and
    if the customer leaves the geo-fenced, physical retail location, uninstalling the unpurchased product from the mobile device.

2. The method as defined in claim 1, further comprising:
    if the customer did not make a past inquiry about a product, the retail server node determining if the customer is making a current inquiry about a product; and
    in response to the current inquiry, the retail server node pushing the product to the mobile device of the customer based on information associated with the current inquiry.

3. The method as defined in claim 1, further comprising storing at least one of a group comprising inquiry information and purchase information.

4. The method as defined in claim 3, wherein storing the inquiry information or purchase information comprises amending a customer activity record including previous customer activity associated with the product to include the inquiry information or purchase information.

5. The method as defined in claim 4, further comprising pushing a cookie to a computer associated with the customer, wherein the cookie stores at least a portion of the customer activity record on the computer.

6. The method as defined in claim 1, wherein the customer's presence is detected by the mobile device registering with the retail server node.

7. The method as defined in claim 6, wherein the retail server node determines an identity of the customer from information received from the mobile device registering with the retail server node.

8. The method as defined in claim 7, wherein the identity of the customer is used to search a customer information database for inquiry information associated with the customer.

9. The method as defined in claim 1, wherein the product is an unpurchased software application.

10. The method as defined in claim 1, wherein pushing the product to the mobile device comprises:
    the retail server node pushing a notice of a software application available for testing to the mobile device;
    the retail server node determining if the customer requests the software application;
    in response to determining that the customer requests the software application, the retail server node pushing the software application and an uninstall application to the mobile device;

the retail server node determining if the customer is still present or has left the geo-fenced, physical retail location ;

if the customer is still present, waiting a period of time; and if the customer has left the geo-fenced, physical retail location , sending a signal to the uninstall application to uninstall the application.

11. A computer program product comprising computer executable instructions stored onto a non-transitory computer readable medium which, when executed by a processor of a computer, causes the processor to execute a method for providing a software application, that the customer has yet to purchase, to a customer while a customer is in a geo-fenced, physical retail location, the method comprising:

a retail server node detecting that a mobile device associated with a customer is present in the geo-fenced, physical retail location based on a Global Positioning System ("GPS") location;

in response to detecting the mobile device, the retail server node pushing a notice that the software application is available for testing to the mobile device;

the retail server node determining if the customer requests the software application;

in response to determining that the customer requests the software application, the retail server node pushing the software application and an uninstall application to the mobile device before the customer purchases the software application;

the retail server node determining if the customer is still present or has left the geo-fenced, physical retail location;

if the customer is still present, waiting a period of time then repeating the step of determining if the customer is still present; and if the customer has left the geo-fenced, physical retail location , uninstalling the software application.

12. The computer readable medium as defined in claim 11, wherein the retail server node detects presence by determining if the mobile device entered a geo-fenced retail location.

13. The computer readable medium as defined in claim 12, further comprising registering the customer associated with the mobile device.

14. The computer readable medium as defined in claim 11, further comprising:

the retail server node sending a periodic heartbeat signal to the mobile device;

wherein, the periodic heartbeat signal is received by the mobile device only within the geo-fenced, physical retail location, and wherein, if the mobile device stops receiving the periodic heartbeat signal, the uninstall application uninstalls the software application from the mobile device.

15. The computer readable medium as defined in claim 11, further comprising:

the retail server node receiving a periodic heartbeat signal from the mobile device;

wherein, the retail server node receives the periodic heartbeat signal from the mobile device only within a geo-fenced area, and wherein, if the retail server node stops receiving the periodic heartbeat signal, the retail server node sends a signal to the uninstall application to uninstall the software application from the mobile device.

* * * * *